US008845541B2

(12) United States Patent
Strunk et al.

(10) Patent No.: US 8,845,541 B2
(45) Date of Patent: Sep. 30, 2014

(54) ULTRASONIC MEDICAL DEVICE WITH TORQUE LIMITING FRANGIBLE LINK HINGE

(71) Applicant: Cybersonics, Inc., Erie, PA (US)

(72) Inventors: Jon Gregory Strunk, Auburn Hills, MI (US); Jeffrey J. Vaitekunas, Erie, PA (US); Jeremy Louis Hemingway, Cincinnati, OH (US)

(73) Assignee: Cybersonics, Inc., Erie, PA (US)

( * ) Notice: Subject to any disclaimer, the term of this patent is extended or adjusted under 35 U.S.C. 154(b) by 134 days.

(21) Appl. No.: 13/652,072

(22) Filed: Oct. 15, 2012

(65) Prior Publication Data

US 2013/0096470 A1    Apr. 18, 2013

Related U.S. Application Data

(60) Provisional application No. 61/547,276, filed on Oct. 14, 2011.

(51) Int. Cl.
*A61B 8/00* (2006.01)
*A61B 17/22* (2006.01)
*A61B 17/00* (2006.01)

(52) U.S. Cl.
CPC ... *A61B 17/22004* (2013.01); *A61B 2017/0046* (2013.01); *A61B 2017/22015* (2013.01)
USPC ................... 600/459; 601/2; 601/3; 600/462

(58) Field of Classification Search
USPC .................................. 600/459, 462; 601/2, 3
See application file for complete search history.

(56) References Cited

U.S. PATENT DOCUMENTS 4,669,999 A * 6/1987 Miller ............................ 464/10
2012/0116262 A1 * 5/2012 Houser et al. ..................... 601/2

* cited by examiner

*Primary Examiner* — Unsu Jung
*Assistant Examiner* — Rajeev Siripurapu
(74) *Attorney, Agent, or Firm* — Ulmer & Berne LLP

(57) ABSTRACT

An ultrasonic medical device can include a transducer, a coupling system, and a waveguide. The coupling system can be configured to attach and adequately torque the waveguide to the transducer for use in a medical procedure. The coupling system can be configured to detach the inner probe from the transducer upon completion of the medical procedure.

17 Claims, 16 Drawing Sheets

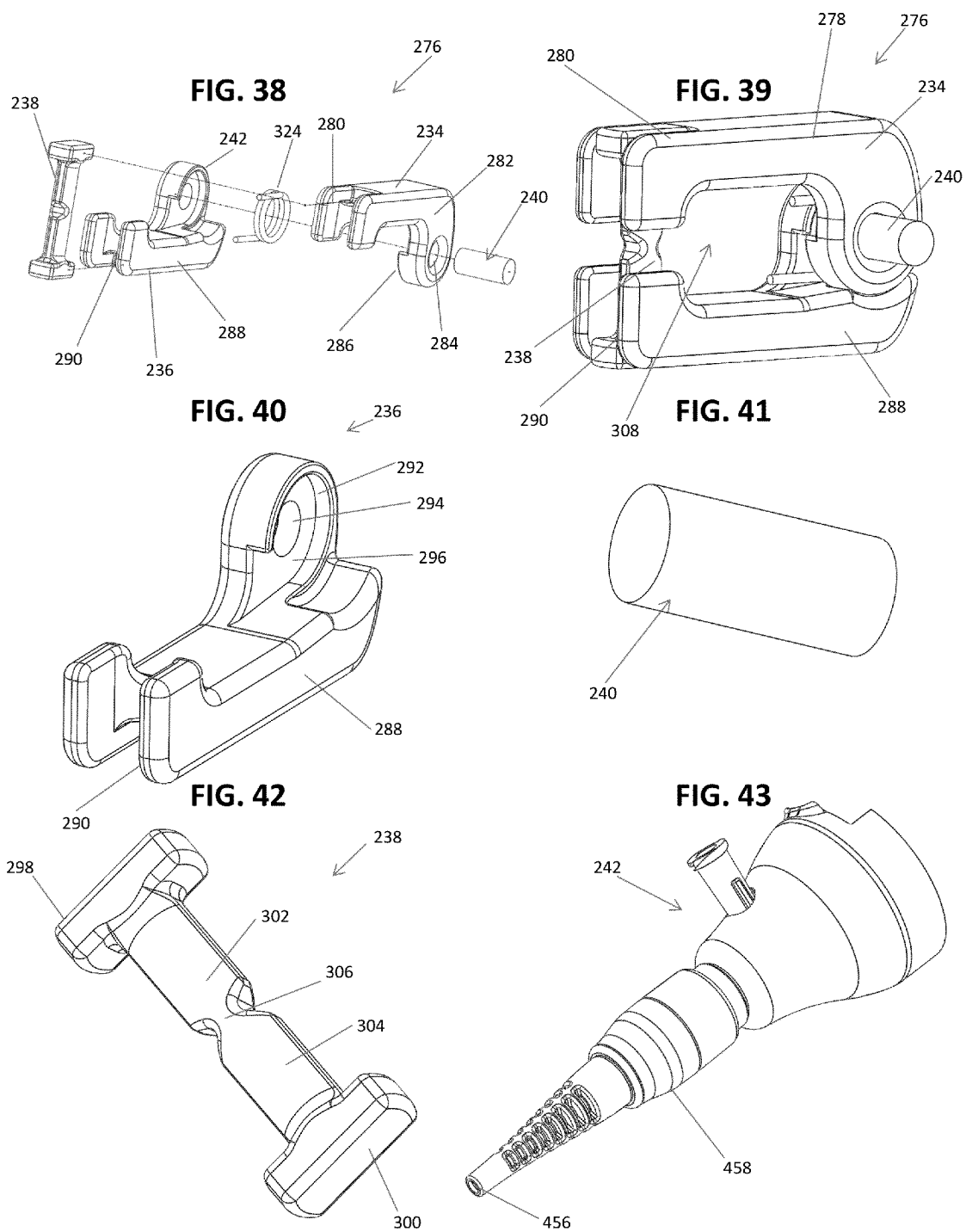

ULTRASONIC MEDICAL DEVICE WITH TORQUE LIMITING FRANGIBLE LINK HINGE

REFERENCE TO RELATED APPLICATION

The present application claims priority of U.S. provisional application Ser. No. 61/547,276, filed Oct. 14, 2011, and hereby incorporates this application herein by reference in its entirety.

TECHNICAL FIELD

This application relates generally to a surgical instrument for disintegrating tissue and more particularly to percutaneous surgical instruments for use in urological lithotripsy or vascular applications.

BACKGROUND

Many people develop calculi within their biliary, urinary, renal, or urethral systems. Such calculi may block ducts and/or cause great pain and therefore must be removed. Various devices are known that are capable of de-bulking such calculi. Such devices can include ultrasonic fixed probe devices that can be configured to operate at frequencies in a low 20-30 kHz range and pneumatic impact probes that can be configured to deliver high energy at lower frequencies. Many people also develop potentially life threatening atherosclerosis due to the build up of plaque within the vasculature, the removal or reduction of which can have significant health benefits.

SUMMARY

In accordance with one embodiment, an ultrasonic medical device can comprise a transducer, an inner probe, and a coupling system. The transducer can be configured to convert an electrical drive signal to mechanical motion at an ultrasonic frequency, where the transducer can have a first connector. The waveguide can have a proximal end and a distal end, where the proximal end can have a second connector that can be configured to mate with the first connector, where the waveguide can be configured to receive the mechanical motion from the transducer and can propagate the mechanical motion along the waveguide. The coupling system can comprise a frangible link, where the coupling system can be configured to attach the second connector of the waveguide to the first connector of the transducer, where the frangible link can be fractured when a predetermined torque limit is reached.

In accordance with one embodiment, an ultrasonic medical device can comprise a transducer, an inner probe, and a coupling system. The transducer can be configured to convert an electrical drive signal to mechanical motion at an ultrasonic frequency, where the transducer can have a first connector. The waveguide can have a proximal waveguide end and a distal waveguide end, where the proximal waveguide end can have a second connector configured to mate with the first connector, where the waveguide can be configured to receive the mechanical motion from the transducer and can propagate the mechanical motion along the waveguide. The coupling system can comprise a hinge assembly, where the hinge assembly can be configured to torque the second connector of the waveguide to the first connector of the transducer, where the hinge assembly can be configured to transition from a first position to a second position when a predetermined torque limit is reached.

In accordance with one embodiment, an ultrasonic medical device can comprise a transducer, an inner probe, and a coupling system. The transducer can be configured to convert an electrical drive signal to mechanical motion at an ultrasonic frequency, where the transducer can have a first connector. The waveguide can have a proximal waveguide end and a distal waveguide end, where the proximal waveguide end can have a second connector that can be configured to mate with the first connector, where the waveguide can be configured to receive the mechanical motion from the transducer and can propagate the mechanical motion along the waveguide. The coupling system can comprise a hinge assembly having a frangible link, where the hinge assembly can be configured to torque the second connector of the waveguide to the first connector of the transducer, where the hinge assembly can be configured to transition from a first position to a second position when the frangible link is fractured.

BRIEF DESCRIPTION OF THE DRAWINGS

It is believed that certain embodiments will be better understood from the following description taken in conjunction with the accompanying drawings in which:

FIG. 38 is an exploded view of a portion of the coupling system of FIG. 32, namely the hinge assembly illustrated in FIG. 33.

FIG. 39 is a perspective view of a portion of the coupling system of FIG. 32, namely the hinge assembly illustrated in FIG. 33.

FIG. 40 is a perspective view of a portion of the coupling system of FIG. 32, namely the first arm illustrated in FIG. 32.

FIG. 41 is a perspective view of a portion of the coupling system of FIG. 32, namely the pin illustrated in FIG. 32.

FIG. 42 is a perspective view of a portion of the coupling system of FIG. 32, namely the torque transmission element illustrated in FIG. 32.

FIG. 43 is a perspective view of a portion of the coupling system of FIG. 32, namely the top housing illustrated in FIG. 32.

DETAILED DESCRIPTION

Figure 1:
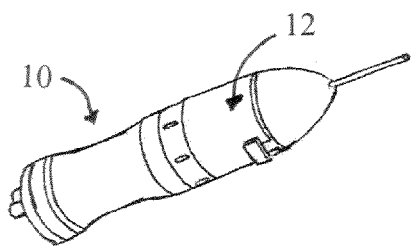
FIG. 1 is a perspective view of an ultrasonic medical device according to one embodiment.
Figure 2:
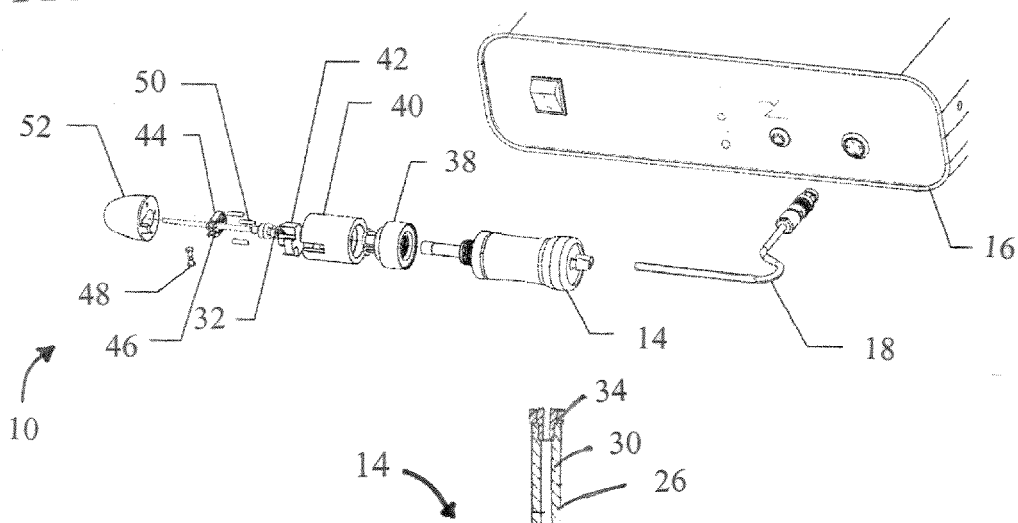
FIG. 2 is an exploded view of the ultrasonic medical device of FIG. 1, shown in association with a cable and a generator.

FIGS. 1 and 2 depict an ultrasonic medical device 10 according to one embodiment. The ultrasonic medical device 10 can include a coupling system 12 and a transducer 14. The ultrasonic medical device 10 can be configured to connect to a generator 16 with an electric cable 18 to delivery any suitable ultrasonic frequency for use in vascular applications, lithotripsy applications, or for any other suitable purpose.

Figure 3:
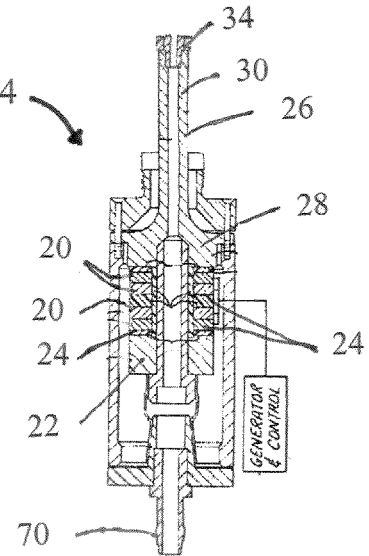
FIG. 3 is a cross-sectional view of a transducer according to one embodiment.

FIG. 3 depicts the transducer 14 according to one embodiment. The transducer 14 can be configured to produce vibrations at ultrasonic frequencies, which can be formed from a plurality of piezoelectric crystals (not shown) or magnetostrictive assembly 20 and a back plate 22. The magnetostrictive assembly 20 can include insulators 24 between the piezoelectric crystals to overcome an interference effect on other instruments. The vibrations can be amplified by a horn 26, which can be coupled to the transducer 14 at a first end 28 and can be configured to receive an inner probe 32 at a second end 30. According to one embodiment, the second end 30 of the horn 26 can include a connector 34 having internal threads, which can be configured to mate and engage a connector (not shown) having a threaded portion 36 on the inner probe 32.

Figure 4:
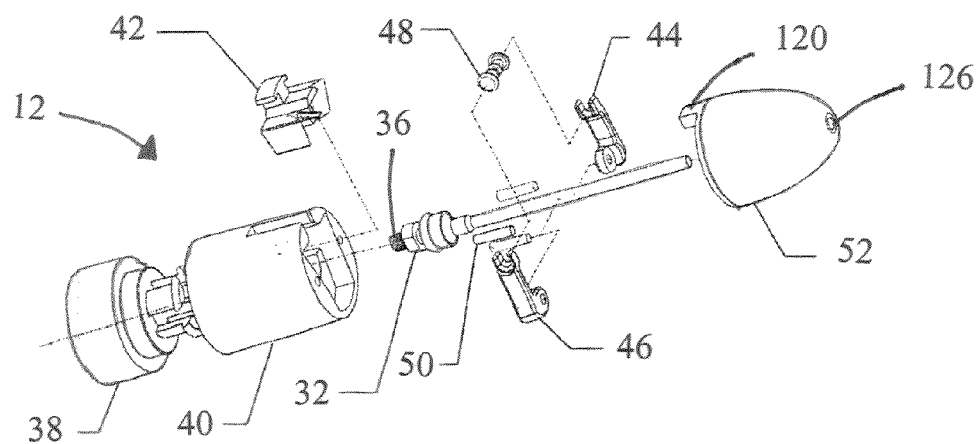
FIG. 4 is an exploded view of a coupling system according to one embodiment, with the coupling system including a transducer coupling, a middle housing, a lock, an inner probe, a first arm, a second arm, a torque transmission element, a pin, and a top housing.
Figure 5:
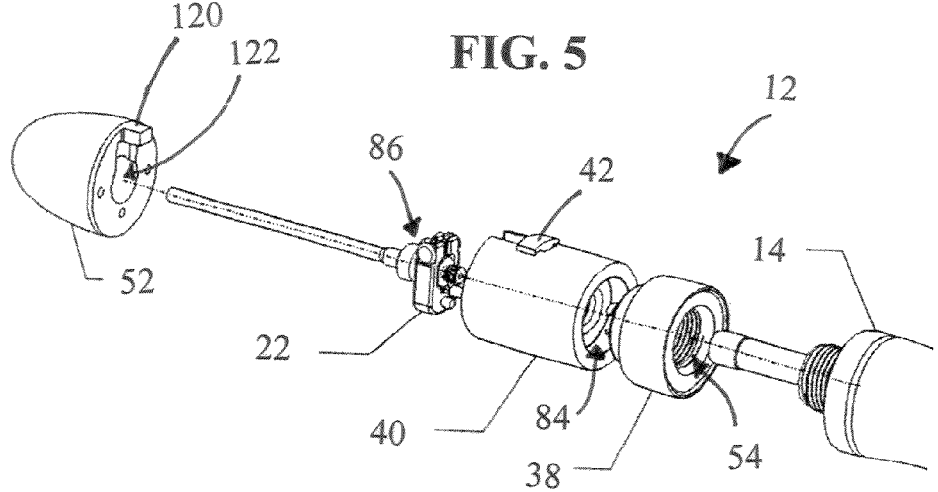
FIG. 5 is an exploded view of the coupling system of FIG. 4, where the lock is shown positioned in the middle housing, and where the first arm, the second arm, the torque transmission element, and the pin are depicted as a hinge assembly.
Figure 6:
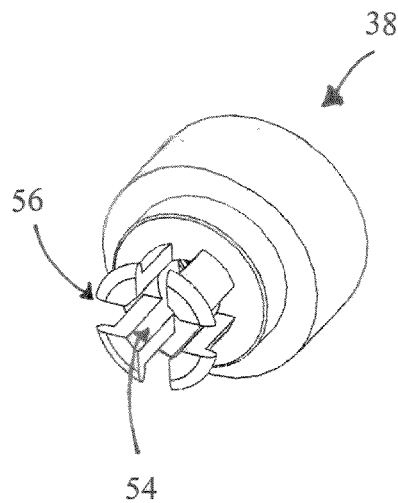
FIG. 6 is a perspective view of a portion of the coupling system of FIG. 4, namely the transducer coupling illustrated in FIG. 4.

FIGS. 4 and 5 depict the coupling system 12 according to one embodiment. The coupling system 12 can include a transducer coupling 38, a middle housing 40, a lock 42, an inner probe 32, a first arm 44, a second arm 46, a torque transmission element 48, at least one pin 50, and a top housing 52. The transducer coupling 38, also shown in FIG. 6, can define a substantially cylindrical first cavity 54 through which the second end 30 of the horn 26 can pass. The transducer coupling 38 can be coupled to the middle housing 40 with a first snap fit coupling 56. The first snap fit coupling 56 can sufficiently secure the transducer coupling 38 to the middle housing 40 such that the middle housing 40 can rotate relative to the transducer coupling 38.

Figure 7:
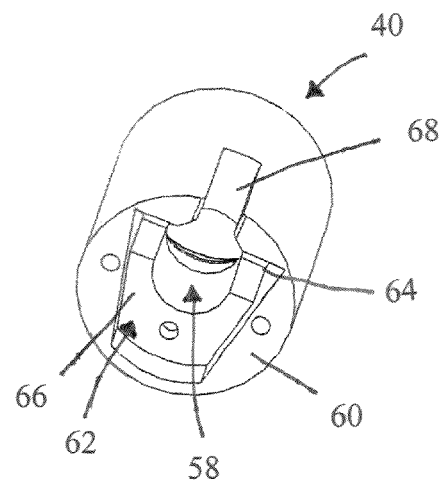
FIG. 7 is a perspective view of a portion of the coupling system of FIG. 4, namely the middle housing illustrated in FIG. 4.

FIG. 7 depicts the middle housing 40 according to one embodiment. As shown in FIG. 7, the middle housing 40 can define a substantially cylindrical second cavity 58, wherein the second cavity 58 can be aligned with the first cavity 54. A top portion 60 of the middle housing 40 can define a recess 62, and in one embodiment, the recess 62 can include at least a first level 64 and a second level 66. The top portion 60 of the middle housing 40 can define a slot 68 configured to receive at least a portion of the lock 42.

Figure 8:
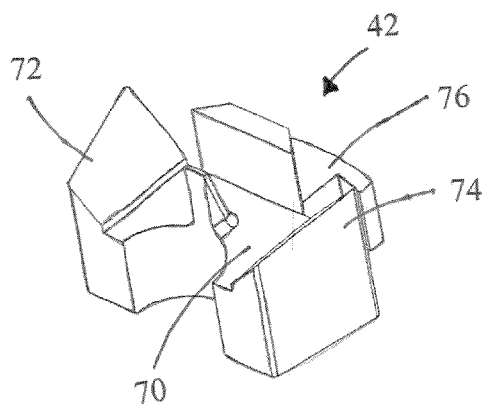
FIG. 8 is a perspective view of a portion of the coupling system of FIG. 4, namely the lock illustrated in FIG. 4.

The lock 42, as shown in FIG. 8, can be configured for insertion in the recess 62 of the middle housing 40. The lock 42 can include a top surface 70, a first wing 72, a second wing 74, and a tab 76, which can be configured to extend through the slot 68 of the middle housing 40. The lock 42 can be positioned at the first level 64 of the recess 62 in a lowered or first position and can be configured for axial movement within the middle housing 40 to an advanced or second position. The lock 42 can be moved from the first position to the second position, and from the second position to the first position, by a user actuating the tab 76 projecting through the slot 68 on the middle housing 40. Advancing the lock 42 from the first position to the second position can engage the hinge assembly 86 as described herein.

Figure 9:
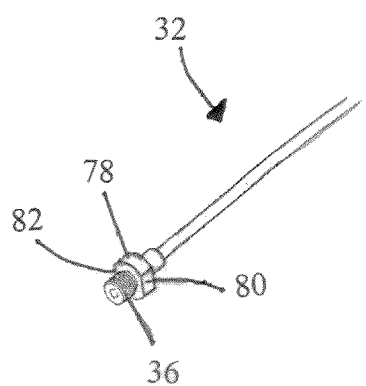
FIG. 9 is a perspective view of a portion of the coupling system of FIG. 4, namely the inner probe illustrated in FIG. 4.

FIG. 9 depicts an inner probe 32 according to one embodiment. The inner probe 32 can include a flange 78, the flange 78 having a first face 80 and a second face 82. The first face 80 and the second face 82 can be substantially parallel. The inner probe 32 can engage the second end 30 of the horn 26 such that the inner probe 32 passes through the first cavity 54 and second cavity 58, where the inner probe 32 can be configured to transmit ultrasonic vibration.

Figure 10:
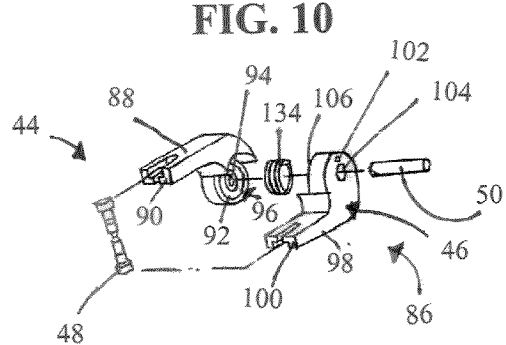
FIG. 10 is an exploded view of a portion of the coupling system of FIG. 4, namely the hinge assembly illustrated in FIG. 5.
Figure 11:
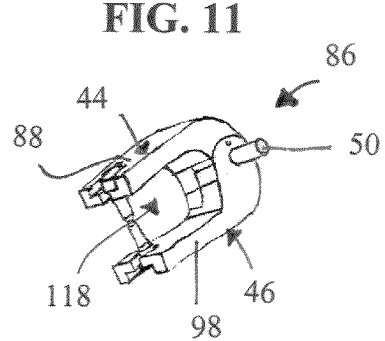
FIG. 11 is a perspective view of a portion of the coupling system of FIG. 4, namely the hinge assembly illustrated in FIG. 5.

Referring to FIGS. 10 and 11, the hinge assembly 86 can include first arm 44, second arm 46, torque transmission element 48, and at least one pin 50. A spring 134 can be positioned within the first arm 44 and the second arm 46 to bias the first arm 44 and the second arm 46 radially outward. The hinge assembly 86 can be positioned within the recess 62 of the middle housing.

Figure 12:
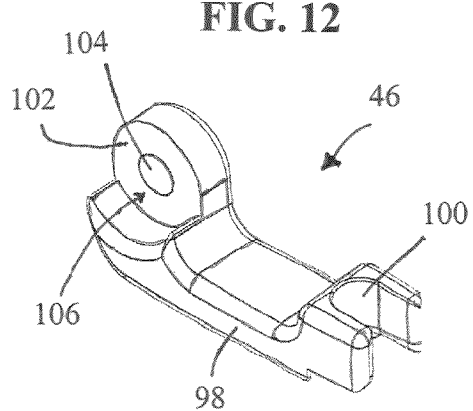
FIG. 12 is a perspective view of a portion of the coupling system of FIG. 4, namely the first arm illustrated in FIG. 4.
Figure 13:
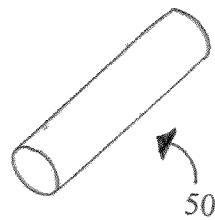
FIG. 13 is a perspective view of a portion of the coupling system of FIG. 4, namely the pin illustrated in FIG. 4.

FIG. 12 depicts the first arm 44 or the second arm 46 of the hinge assembly 86 according to one embodiment. The first arm 44 and the second arm 46 can be substantially identical such that they can be engaged to form a hinge. The first arm 44 can include a first elongated portion 88, a first fork 90, and a first ring 92, which can define a first aperture 94 and a first seat 96. Similarly, the second arm 46 can include a second elongated portion 98, a second fork 100, and a second ring 102, which can define a second aperture 104 and a second seat 106. As shown in FIG. 10, the first seat 96 can be configured to receive the second ring 102 and the second seat 106 can be configured to receive the first ring 92 such that the first aperture 94 can be substantially aligned and coaxial with the second aperture 104. The spring 134 can be positioned within the first arm 44 and the second arm 46. Pin 50 can be inserted through the first aperture 94 and the second aperture 104 to couple the first arm 44 and the second arm 46, where the pin 50 can be configured as a pivot about which the first arm 44 and the second arm 46 can move relative to one another from a first closed position to a second open or expanded position.

Figure 14:
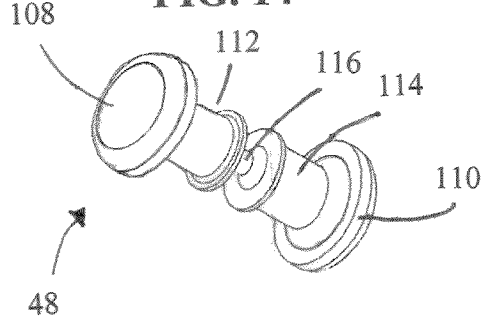
FIG. 14 is a perspective view of a portion of the coupling system of FIG. 4, namely the torque transmission element illustrated in FIG. 4.

The hinge assembly 86 can be biased by the spring 134 toward the open position, where the torque transmission element 48, shown in FIG. 14, can retain the hinge assembly 86 in the closed position until such time as the torque transmission element 48 is fractured. As shown in FIGS. 10 and 14, the torque transmission element 48 can include a first plate 108, a second plate 110, a first connecting rod 112, a second connecting rod 114, and a frangible member 116. The frangible member 116 can be positioned between the first connecting rod 112 and the second connecting rod 114 as shown in FIG. 14 and can couple the first connecting rod 112 and the second connecting rod 114 until such time as the frangible member 116 is fractured. In one embodiment, as shown in FIGS. 5 and 11, the first fork 90 can receive the first connecting rod 112 and the second fork 100 can receive the second connecting rod 114 such that the first plate 108 and the second plate 110 can restrict the first arm 44 and the second arm 46 from pivoting to the open position. It will be appreciated any suitable coupling may be provided to retain the hinge assembly 86 in a closed position where, for example, the torque transmission element can be part of a unitary construction with the hinge assembly 86.

As shown in FIG. 11, the hinge assembly 86 can initially be provided in the closed position, where the first arm 44, the second arm 46, and the frangible member 116 can define a gap 118 through which the inner probe 32 can pass. The hinge assembly 86, when in the closed position, can be configured to engage the flange 78 of the inner probe 32, such that the first elongated portion 88 of the first arm 44 and the second elongated portion 98 of the second arm 46 can engage the first face 80 of the flange 78 and the second face 82 of the flange 78, respectively. The hinge assembly 86 can be positioned relative to the flange 78 on the inner probe 32 such that rotation of hinge assembly 86 correspondingly rotates the inner probe 32.

Figure 15:
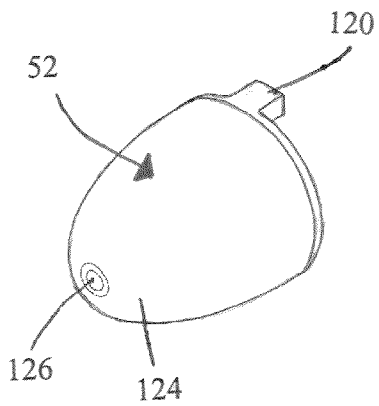
FIG. 15 is a perspective view of a portion of the coupling system of FIG. 4, namely the top housing illustrated in FIG. 4.

The middle housing 40 can be coupled to the top housing 52 with a second snap fit coupling 120. As shown in FIG. 5, the top housing 52 can define a third cavity 122 through which the inner probe 32 can pass. The third cavity 122 can be substantially aligned with the first cavity 54 and the second cavity 58. As shown in FIG. 15, the upper portion 124 of the top housing 52 can define an orifice 126 through which the inner probe 32 can pass.

Figure 16:
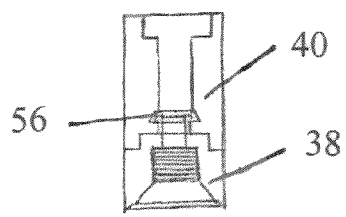
FIG. 16 is a cross-sectional view depicting a portion of the coupling system of FIG. 4, namely the transducer coupling and the middle housing illustrated in FIG. 4, with the middle housing being depicted to engage the transducer coupling.
Figure 17:
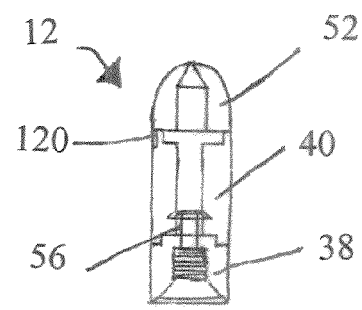
FIG. 17 is a cross-sectional view depicting a portion of the coupling system of FIG. 4, namely the transducer coupling, the middle housing, and the top housing illustrated in FIG. 4, with the top housing being depicted to engage the middle housing.

To assemble the coupling system 12, the transducer coupling 38 can be coupled to the middle housing 40 with the first snap fit coupling 56, as shown in FIG. 16. As set forth above, the first snap fit coupling 56 can secure the transducer coupling 38 to the middle housing 40 such that the middle housing 40 can rotate relative to the transducer coupling 38. The lock 42 can be inserted into the middle housing 40 with the inner probe 32 and the hinge assembly 86 in the closed position. As shown in FIG. 17, the middle housing 40 can be coupled to the top housing 52 with the second snap fit coupling 120 such that the inner probe 32 can pass through the orifice 126.

Figure 18:
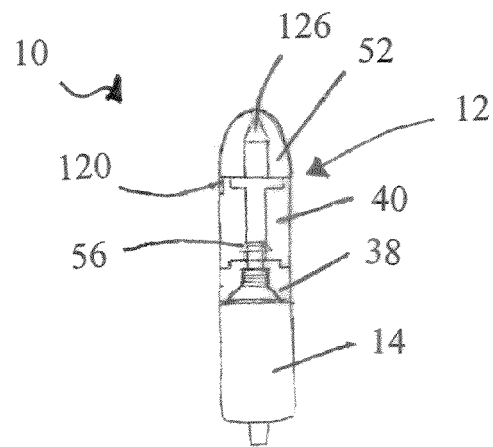
FIG. 18 is a cross-sectional view depicting a portion of the coupling system of FIG. 4, namely the transducer coupling, the middle housing, and the top housing illustrated in FIG. 4, with the transducer coupling being depicted to engage a transducer.
Figure 19:
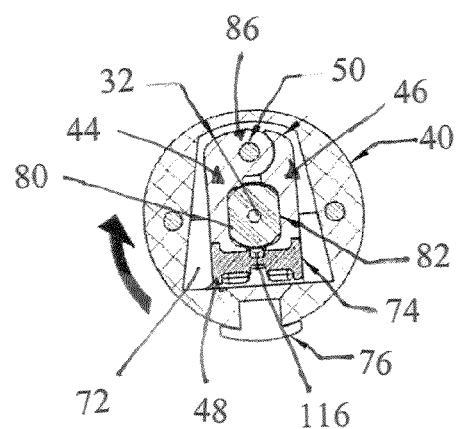
FIG. 19 is a top cross-sectional view of the coupling system of FIG. 4, shown with a rotational force applied to the middle housing and the first arm and the second arm being depicted in a closed position.

As shown in FIG. 18, the coupling system 12 can be coupled to the transducer 14. In one embodiment, the transducer coupling 38 can be configured to threadedly engage the transducer 14. As described herein, the second end 30 of the horn 26 can pass through the first cavity 54, through the bottom opening 84 of the middle housing 40, and into the second cavity 58, where the second end 30 of the horn 26 can be positioned to engage the inner probe 32. The middle housing 40, which can be coupled to the top housing 52, can rotate relative to the transducer coupling 38 such that the second end 30 of the horn 26 can threadedly engage the inner probe 32, as shown in FIG. 19. In one embodiment, rotating the middle housing 40 correspondingly rotates the hinge assembly 86, where rotating the hinge assembly correspondingly rotates the inner probe 32 such that the inner probe 32 is threadedly engaged with the horn 26. In one embodiment, rotation of the middle housing can threadly engage the inner probe 32 until there is sufficient torque on the hinge assembly 86 to defeat, fracture, or disengage the frangible member 116. Once the frangible member 116 is defeated, the first arm 44 and the second arm 46 of the hinge assembly 86 can expand radially outward to the open position such that rotation of the middle housing 40 no longer correspondingly rotates the inner probe 32.

Figure 20:
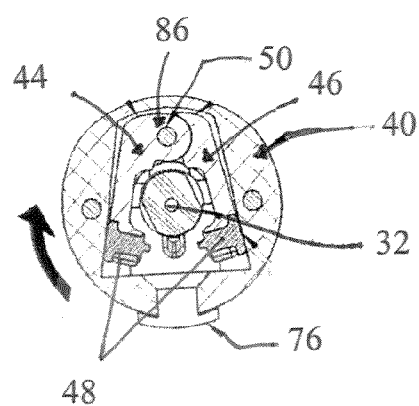
FIG. 20 is a top cross-sectional view of the coupling system of FIG. 4, shown with the torque transmission element shown fractured and the first arm and the second arm extended radially outward into an open position.
Figure 21:
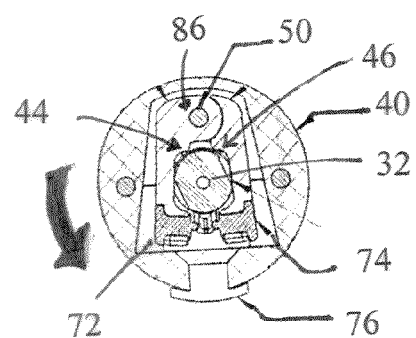
FIG. 21 is a top cross-sectional view of the coupling system of FIG. 4, shown with the hinge assembly retracted to a closed position.

FIGS. 19-21 depict one embodiment of a method for securing the inner probe 32 to the horn 26 with a predetermined amount of torque. Providing a torque limiting system and method can provide for a secure attachment between the inner probe 32 and the horn 26. FIG. 19 depicts the hinge assembly 86 in a closed position as a user rotates the middle housing 40. With the hinge assembly 86 in the closed position and engaging the flange 78 of the inner probe 32, rotation of the middle housing can threadedly couple the inner probe to the horn 26. The inner probe 32 can be torqued by the hinge assembly 86 and middle housing until a predetermined torque limit is reached, at which point the frangible member 116 is defeated, as shown in FIG. 20.

When the frangible member 116 is defeated, first arm 44 and the second arm 46 of the hinge assembly 86 can pivot away from the inner probe 32 to the open position, as shown in FIG. 20, such that rotation of the middle housing 40 no longer torques the inner probe 32. In one embodiment, the frangible member 116 is configured to break or otherwise be defeated at a level of torque corresponding to a suitable connection between the inner probe 32 and the horn 26. In this manner, the inner probe 32 can be securely attached to the horn 26 without relying upon a user to make a determination as to whether the components of the ultrasonic medical device 10 are suitably engaged. As shown in FIG. 20, the hinge assembly 86 in the open position can have the first arm 44 and the second arm 46 spaced apart such that the arms do not contact the inner probe 32 during use of the ultrasonic medical device 10. The second cavity 58 can be sized to allow the first arm 44 and the second arm 46 to expand radially such that they do not contact the inner probe 32, where contact between the arms and the inner probe 32 may interfere with the transmission of ultrasonic vibration.

After use of the ultrasonic medical device 10, for example in a lithotripsy or vascular procedure, the coupling system 12 can be removed from the transducer 14. As shown in FIG. 21, with the frangible member 116 defeated, the hinge assembly 86 can be returned to the closed position from the open position with the lock 42, as described herein, such that the hinge assembly 86 can reengage the flange 78 on the inner probe 32. Once the hinge assembly 86 is reengaged with the inner probe 32, the middle housing can be rotated to decouple the inner probe from the transducer 14.

Figure 22:
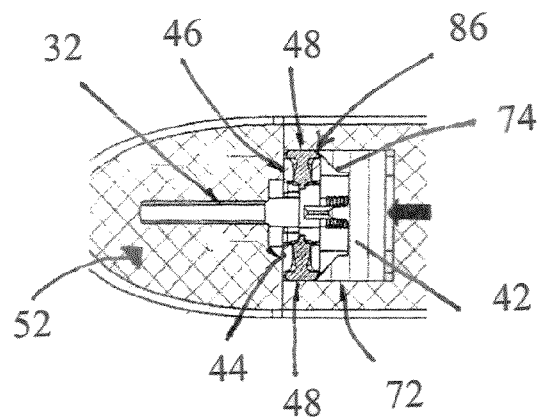
FIG. 22 is a cross-sectional view of the coupling system of FIG. 4, shown with the lock being depicted in a lowered or disengaged position and the hinge assembly being depicted in an open position where the first arm and the second arm are extended radially outward.
Figure 23:
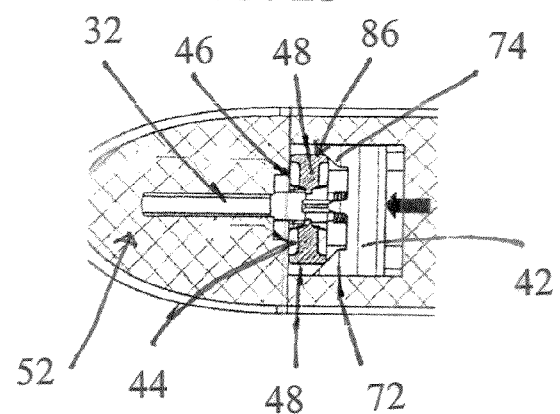
FIG. 23 is a cross-sectional view of the coupling system of FIG. 4, shown with the lock partially advanced to engage the first arm and the second arm.
Figure 24:
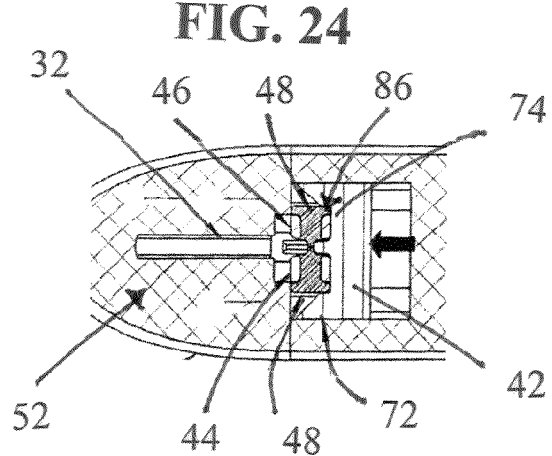
FIG. 24 is a cross-sectional view of the coupling system of FIG. 4, shown with the lock fully engaged with the hinge assembly such that the hinge assembly is urged into a closed position.
Figure 25:
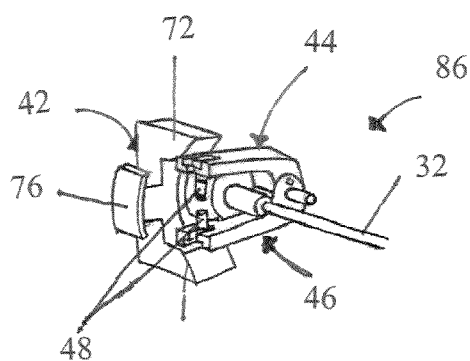
FIG. 25 is a perspective view of a portion of the coupling system of FIG. 4, shown with the lock partially engaging the first arm and the second arm to urge the first arm and the second arm radially inward.

FIGS. 22-24 describe one embodiment of a method for using the lock 42 to return the hinge assembly 86 to the closed position and decouple the inner probe 32 from the transducer 14. In FIG. 22, the frangible member 116 is shown defeated with the hinge assembly 86 in the open position, where the lock 42 is shown in the disengaged or lowered position. In one embodiment, the tab 76 can be urged laterally by, for example, the finger of a user, to move the lock 42 from the lowered position to a position where the lock 42 engages the hinge assembly 86. As shown in FIGS. 23 and 25, the lock 42 can be urged towards the engaged position, where the first wing 72 of the lock 42 and the second wing 74 of the lock 42 can engage the first arm 44 and the second arm 46, respectively. The first wing 72 and the second wing 74 can be angled such that the first arm 44 and the second arm 46 can be drawn inward as the lock 42 is advanced. The lock 42 can be moved to a fully raised or engaged position, as shown in FIG. 24, where the first arm 44 and the second arm 46 of the hinge assembly 86 are fully retracted. When the hinge assembly 86 is secured in the closed position by the lock 42, the middle housing 40 can be rotated to remove the inner probe 32 from the transducer 14. In one embodiment, the middle housing 40 is rotated clockwise to couple the inner probe 32 with the transducer 14 and the middle housing 40 is rotated counter-clockwise to decouple the inner probe 32 from the transducer.

Figure 26:
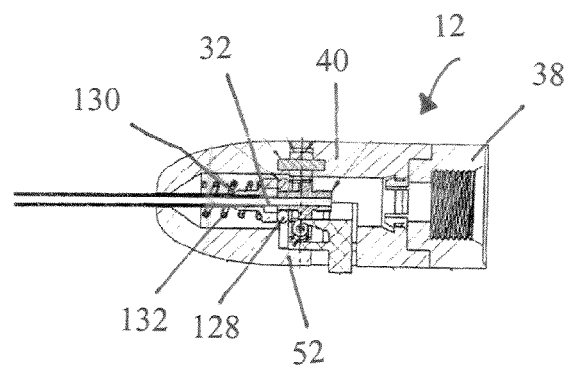
FIG. 26 is a cross-sectional view of the coupling system of FIG. 4, shown in association with a free mass, an outer probe, and a spring.
Figure 27:
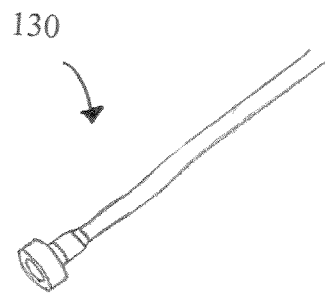
FIG. 27 is a perspective view of a portion of the coupling system of FIG. 4, namely the outer probe illustrated in FIG. 27.
Figure 28:
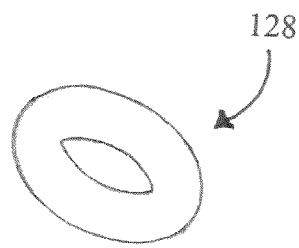
FIG. 28 is a perspective view of a portion of the coupling system of FIG. 4, namely the free mass illustrated in FIG. 27.

FIG. 26 depicts the coupling system 12 according to one embodiment. The coupling system can include a free mass 128, an outer probe 130, and a probe spring 132. The outer probe 130, which is shown in FIG. 27, can be positioned over the inner probe 32 such that the outer probe 130 can move axially relative to the inner probe 32. The free mass 128, which is shown in FIG. 28, can be positioned between the inner probe 32 and the outer probe 130 such that the free mass 128, in response to vibrations from the transducer 14, can impact the outer probe 130, which in turn can transfer impact forces to calculi or any other suitable structure. Impacts of the outer probe 130 by the free mass 128 can be absorbed by a probe spring 132, which can provide a bias against such movement and can return the outer probe 130 to an original position. Thus, the outer probe 130, which can operate at low frequencies can, for example, break large stones into small pieces, and the inner probe 32 can disintegrate ruptured calculi into finer particles.

The outer probe 130 can enclose a structure or system for introducing fluid into a site of a procedure and can provide a structure or system for aspirating fluid and tissue debris from the site of the procedure. In certain embodiments, the inner probe 32 and the outer probe 130 can help to introduce a drug intravascularly such that the drug can dissolve clots or prevent a recurrence of stenosis. The vibrations of the inner probe 32 and the outer probe 130 can facilitate penetration of anti-thrombogenic agents into the vascular or luminal walls to inhibit restenosis. Such antithrombogenic agents can include heparin, hirudin, hirulog, urokinase, streptokinase, tPA, and similar agents. The ultrasonic medical device 10 can comprise a structure or system for aspiration and irrigation of the site of the procedure. The outer probe 130 can be configured in such a way that it may capture or grasp sections of tissue that can be ablated with the probe.

Figure 29:
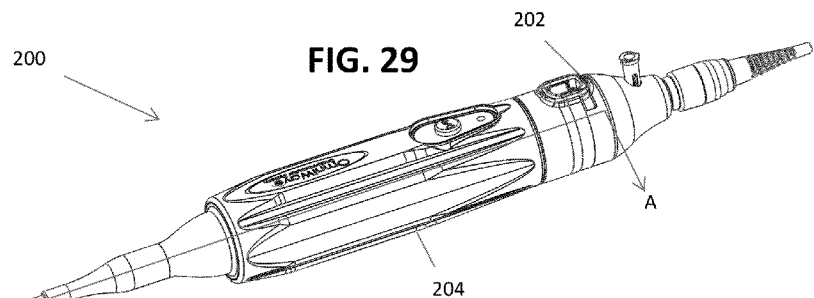
FIG. 29 is a perspective view of an ultrasonic medical device according to an alternate embodiment.
Figure 30:
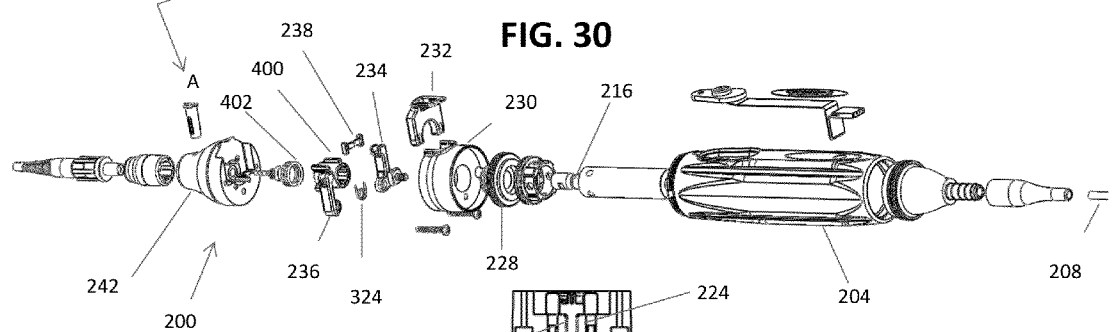
FIG. 30 is an exploded view of the ultrasonic medical device of FIG. 29, further depicting a coupling system and shown in association with a cable.

FIGS. 29 and 30 depict an ultrasonic medical device 200 according to one embodiment. The ultrasonic medical device 200 can include a coupling system 202 and a transducer 204. The ultrasonic medical device 200 can be configured to connect to a generator (such as generator 16 shown in FIG. 2) with an electric cable 208 to deliver any suitable ultrasonic frequency, such as 21 kHz-150 kHz, 21 kHz, 40 kHz, or 40 kHz-150 kHz. It will be appreciated that the generator can provide any suitable dual ultrasonic frequency, such as 40 kHz and 150 kHz. The ultrasonic medical device 200 can be configured for use in vascular applications, lithotripsy applications, percutaneous nephrolithotomy, plaque ablation, thrombectomy, total chronic occlusion crossing, or for any other suitable purpose.

Figure 31:
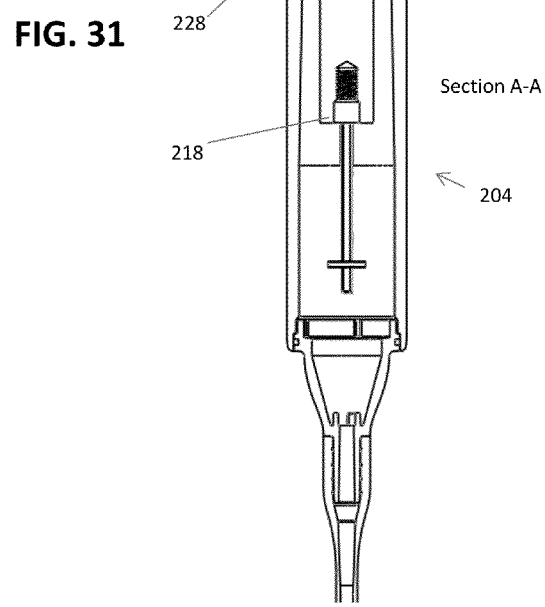
FIG. 31 is a cross-sectional view of a transducer according to one embodiment.

FIG. 31 further depicts a cross-sectional view of the transducer 204. The transducer 204 can be configured to produce vibrations at ultrasonic frequencies, which can be formed from a plurality of piezoelectric crystals (not shown) or a magnetostrictive assembly (not shown.) The transducer 104 can include insulators between the piezoelectric crystals and front and back masses (not shown) to overcome an interference effect on other instruments. Vibrations can be amplified by a horn 216, having a first end 218 and a second end 220, where a waveguide 222 (FIG. 37) can be coupled to the second end 220. The waveguide 222 can be any suitable length such as, for example, from about 50 cm to about 200 cm for a flexible wire waveguide or from about 16 to about 18 inches for a rigid probe waveguide. According to one embodiment, the second end 220 of the horn 216 can include a connector 224 having internal threads, which can be configured to mate and engage a connector 223 (FIG. 37A) having a threaded portion 226 and a pair of flat portions 227 on the waveguide 222. In one example, with reference to FIGS. 37A-37C, the connector 223 of the waveguide 222 can be inserted into a keylock channel 229 defined by the connector 224 on the horn 216. After inserting the connector 223 into the keylock channel 229, the waveguide 222 can be rotated such that the threaded portion 226 engages and couples with the internal threads of the connector 224.

Figure 32:
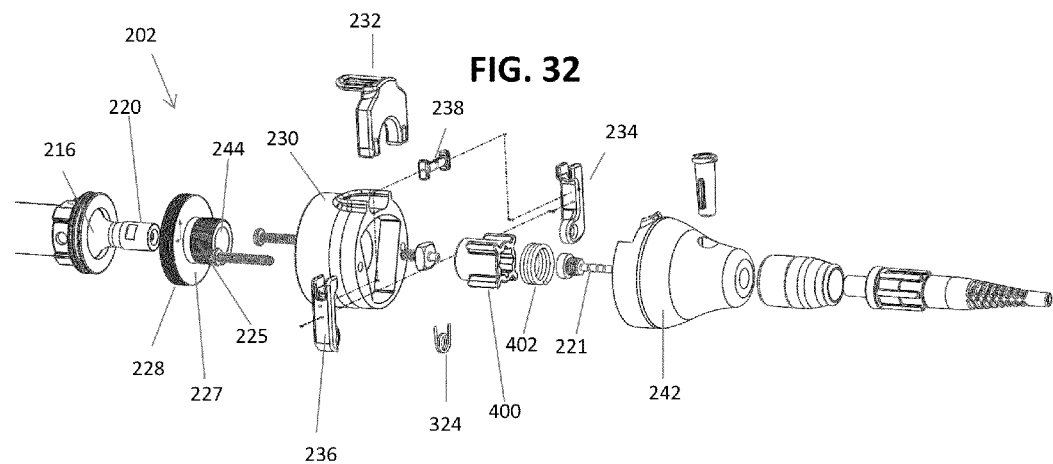
FIG. 32 is an exploded view of a coupling system according to one embodiment, where the coupling system is shown having a transducer coupling, a middle housing, a lock, a wrench, a waveguide, a first arm, a second arm, a torque transmission element, a pin, and a top housing.
Figure 33:
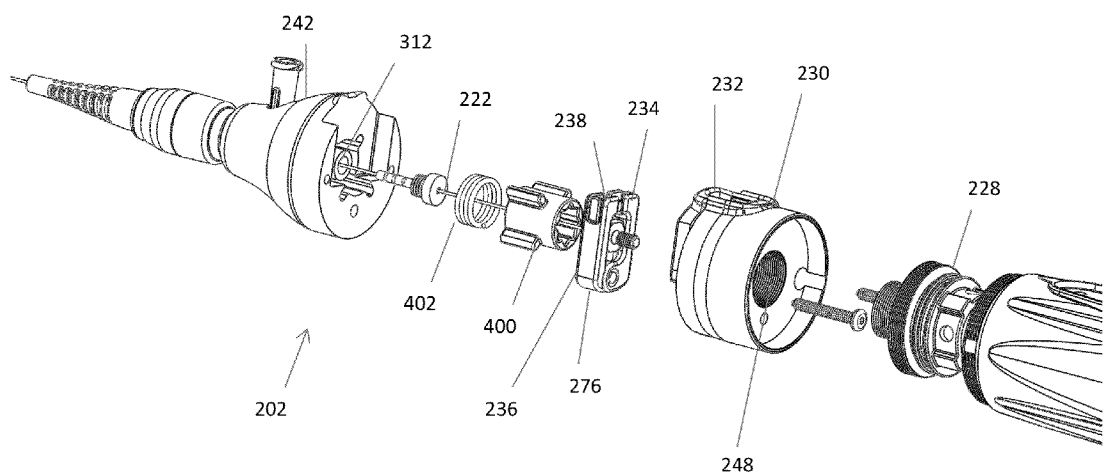
FIG. 33 is an exploded view similar to that of FIG. 32 illustrating a coupling system, where a first arm, a second arm, a torque transmission element, and a pin are depicted as a hinge assembly.

FIGS. 32 and 33 depict the coupling system 202. The coupling system 202 can include a transducer coupling 228, a middle housing 230, a lock 232, a waveguide 222, an acoustic isolation arrangement 221, a first arm 234, a second arm 236, a frangible link 238, at least one pin (FIG. 38), and a top housing 242. The transducer coupling 228 can define a substantially cylindrical first cavity 244 through which the second end 220 of the horn 216 can pass. The transducer coupling 228 can be coupled to the middle housing 230 with a threaded coupling, a bayonette coupling, or any other suitable coupling arrangement.

Figure 34:
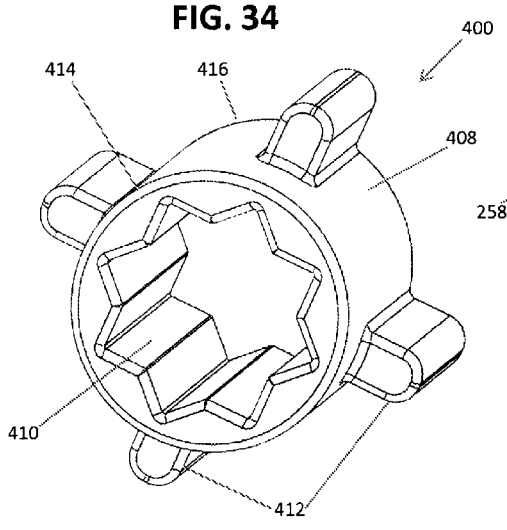
FIG. 34 is a perspective view of a portion of the coupling system of FIG. 32, namely the wrench illustrated in FIG. 32.
Figure 51:
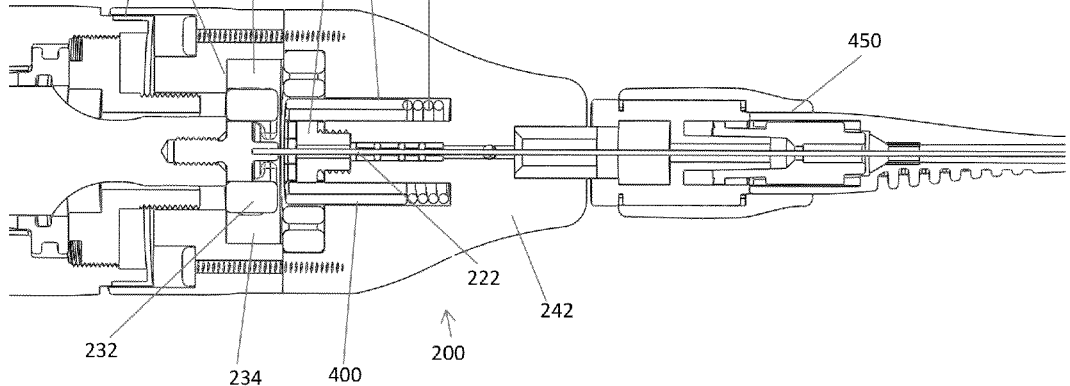
FIG. 51 is a cross-sectional view of the coupling system of FIG. 32, shown with the lock engaged with the ultrasonic medical device to restrict axial movement of the wrench.
Figure 52:
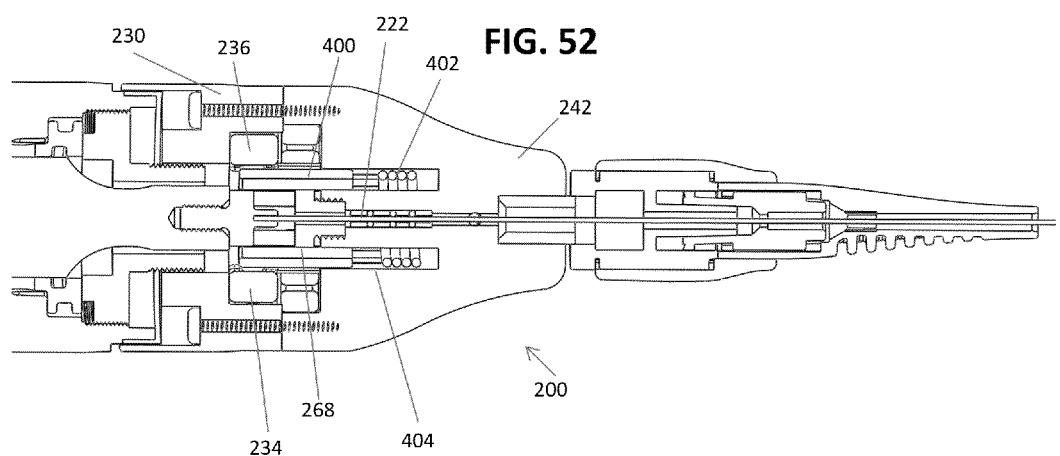
FIG. 52 is a cross-sectional view of the coupling system of FIG. 32, shown with the lock removed and the wrench axially translated to engage the flange of the waveguide.

FIG. 34 illustrates one example of a wrench 400, having a first end 414 and a second end 416. The wrench 400 can include a cylindrical body 408 defining a multi-faceted inner cavity 410, where the inner cavity 410 can be configured to engage the flange 268 of the waveguide 222 (FIG. 37A) such that the waveguide 222 can be removed from the transducer 204 after a procedure is completed. The wrench 400 can include a plurality of radial projections 412 that can be flush with the second end 416 of the wrench 400 and offset from the first end 414 of the wrench 400. As illustrated in FIGS. 51 and 52, the wrench 400 can be housed within a recess 404 that can be defined by the top housing 242.

Figure 35:
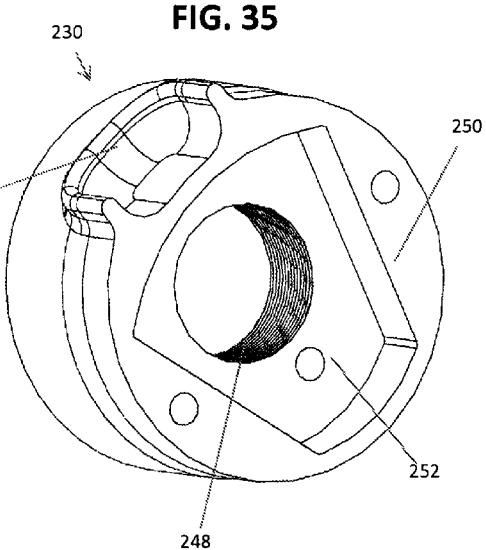
FIG. 35 is a perspective view of a portion of the coupling system of FIG. 32, namely the middle housing illustrated in FIG. 32.

FIG. 35 depicts the middle housing 230 according to one embodiment. As shown in FIG. 35, the middle housing 230 can define a substantially cylindrical threaded second cavity 248, wherein the second cavity 248 can be substantially coaxial with the first cavity 244 (FIG. 32) when the coupling system 202 is assembled. A top portion 250 of the middle housing 230 can define a recess 252 configured to receive the hinge assembly 276 (FIG. 39). The recess 252 can be shaped to retain the frangible link 222 within the first arm 234 and the second arm 236 after the frangible link 222 has been fractured, as described in more detail herein. Recess 252 can be shaped to retain the fractured frangible link 238 halves such that they do not separate from the arms 234, 236 and cause jamming or malfunctioning of the coupling system. The top portion 250 of the middle housing 230 can also define a slot 258 configured to receive at least a portion of the lock 232.

Figure 36:
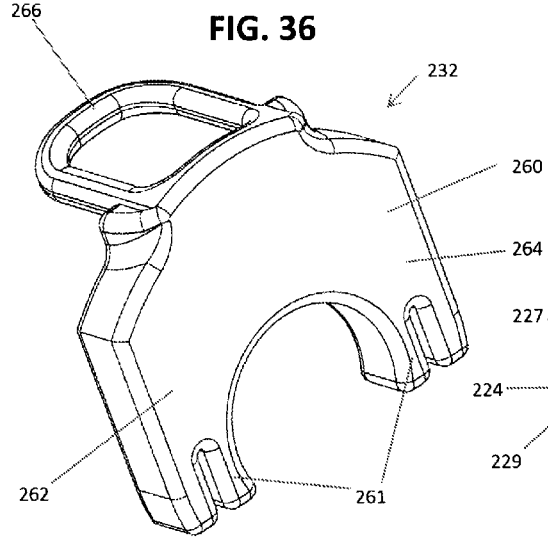
FIG. 36 is a perspective view of a portion of the coupling system of FIG. 32, namely the lock illustrated in FIG. 32.

One example of the lock 232, as shown in FIG. 36, can be configured for placement over the top portion 250 of the middle housing 230 when the coupling system 202 is assembled (FIG. 35) to prevent the wrench 400 from axially translating to engage the flange 268 of the waveguide 222 (FIG. 51). The lock 232 can include a top surface 260, a first wing 262, a second wing 264, and a pair of flexible hinges 261. A tab 266 can be seated in a slot 258 of the middle housing 230, for example, as shown in FIG. 35, such that it can be accessible to a user. As further described herein, the lock 232 can function as a removable barrier, where the lock 232 can be moved from between a first position and a second position to facilitate the engagement or disengagement of the wrench 400 with the flange 268, such that the waveguide 222 can be removed from or attached to the horn 216. The lock 232 can have a generally semi-circular configuration that partially surrounds the cylindrical body 408 of the wrench 400 in the first position. It will be appreciate that other suitable configurations could be employed. In a first position, prior to the lock 232 being removed, the radial projections 412 of the wrench 400 can abut the top surface 260 of the lock 232 to prevent proximal movement of the wrench 400. When the lock 232 is transitioned from the first position to a second position, the living hinges 261 can be moved or flexed radially outward by the cylindrical body 408 of the wrench 400. In one example, the living hinges 261 can prevent the lock 232 from inadvertently being removed from the ultrasonic medical device 200, where sufficient force must be applied to the lock 232 to move the living hinges 261 over the body 408 of the wrench 400 before the lock 232 can be removed.

Figure 37A:
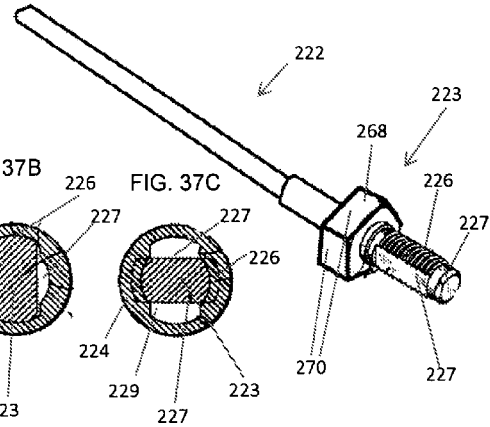
FIG. 37A is a perspective view of a portion of the coupling system of FIG. 32, namely the waveguide shown with a connector having a threaded portion and a pair of flats.
Figure 37B:
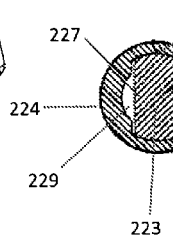
FIG. 37B is cross-sectional view of the connector of FIG. 37A inserted into a keylock channel defined by a horn.
Figure 37C:
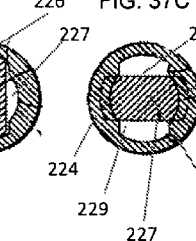
FIG. 37C is a cross-sectional view of the connector of FIG. 37A show rotated within the keylock channel defined by the horn.
Figure 44:
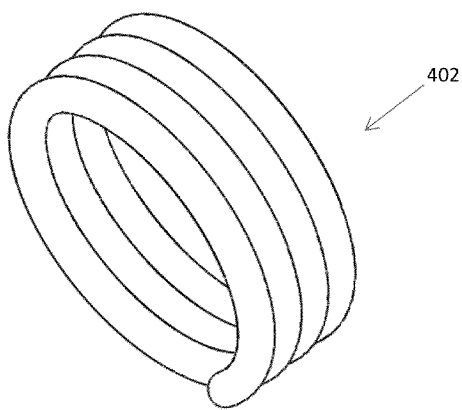
FIG. 44 is a perspective view depicting a portion of the coupling system of FIG. 32, namely a spring in a compressed configuration as shown in FIG. 32.

FIG. 37A depicts a waveguide 222 according to one embodiment. The waveguide 222 can include a flange 268 having a plurality of faces 270 that can, for example, be arranged in a hexagonal configuration such that the flange 268 can mate with the wrench 400 (FIG. 34). It will be appreciated that other suitable configurations could be employed. The connector 223 of the waveguide 222 can engage the connector 224 of the horn 216 (FIG. 32) such that the waveguide 222 can be configured to transmit one or more ultrasonic vibrations.

Referring to FIGS. 38 and 39, one example of a hinge assembly 276 can include a first arm 234, a second arm 236, a frangible link 238, and at least one pin 240 (FIG. 41). A spring 324 can be positioned within the first arm 234 and the second arm 236 to bias the first arm 234 and the second arm 236 radially outward. The hinge assembly 276 can be positioned within the recess 252 of the middle housing 230 (FIG. 35), where the recess 252 can be configured and sized to accept the hinge assembly 276 in an open position and a closed position.

FIGS. 38-40 further depict the first arm 234 and the second arm 236 of the hinge assembly 276. The first arm 234 and the second arm 236 can be substantially identical such that they can be engaged to form a hinge. The first arm 234 can include a first elongated portion 278, a first fork 280, and a first ring 282, which can define a first aperture 284, and a first seat 286. Similarly, the second arm 236 can include a second elongated portion 288, a second fork 290, and a second ring 292, which can define a second aperture 294 and a second seat 296. As shown in FIG. 38, the first seat 286 can be configured to receive the second ring 292 and the second seat 296 can be configured to receive the first ring 282 such that the first aperture 284 can be substantially aligned and coaxial with the second aperture 294. The spring 324 can be positioned within the first arm 234 and the second arm 236. Pin 240 can be inserted through the first aperture 284 and the second aperture 294 to couple the first arm 234 and the second arm 236, where the pin 240 can be configured as a pivot about which the first arm 234 and the second arm 236 can move relative to one another from a first closed position (FIG. 47) to a second open or expanded position (FIG. 48).

The hinge assembly 276 can be biased by the spring 324 toward an open position, where the frangible link 238, shown in FIG. 42, can retain the hinge assembly 276 in the closed position until such time as the frangible link 238 is fractured. As shown in FIGS. 38 and 42, the frangible link 238 can include a first plate 298, a second plate 300, a first connecting rod 302, a second connecting rod 304, and a frangible portion 306. The frangible portion 306 can be positioned between the first connecting rod 302 and the second connecting rod 304 as shown in FIG. 42 and can couple the first connecting rod 302 and the second connecting rod 304 until such time as the frangible portion 306 is fractured or destroyed. In one embodiment, as shown in FIGS. 33 and 39, the first fork 280 can receive the first connecting rod 302 and the second fork 290 can receive the second connecting rod 304 such that the first plate 298 and the second plate 300 can restrict the first arm 234 and the second arm 236 from pivoting to an open position. It will be appreciated that any suitable coupling can be provided to retain the hinge assembly 276 in a closed position where, for example, the frangible link 238 can be part of a unitary construction with the hinge assembly 276.

As shown in FIG. 39, the hinge assembly 276 can initially be provided in the closed position, where the first arm 234, the second arm 236, and the frangible portion 306 can define an aperture 308 through which the waveguide 222 can pass. The hinge assembly 276, when in the closed position, can be configured to engage the flange 268 of the waveguide 222, such that the first elongated portion 278 of the first arm 234 and the second elongated portion 288 of the second arm 236 can engage the faces 270 of the flange 268. The hinge assembly 276 can be positioned relative to the flange 268 on the waveguide 222 such that rotation of hinge assembly 276 can correspondingly rotate the waveguide 222. Rotation of the hinge assembly 276 in the closed position can facilitate coupling the waveguide 222 to the horn 216.

Figure 45:
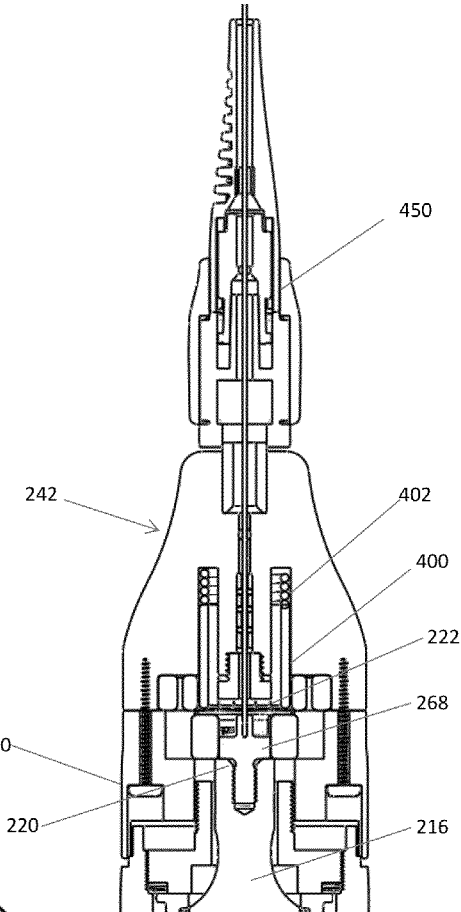
FIG. 45 is a cross-sectional view depicting a portion of the coupling system of FIG. 32, namely the middle housing and the top housing illustrated in FIG. 32, with the top housing shown engaged with the middle housing.
Figure 46:
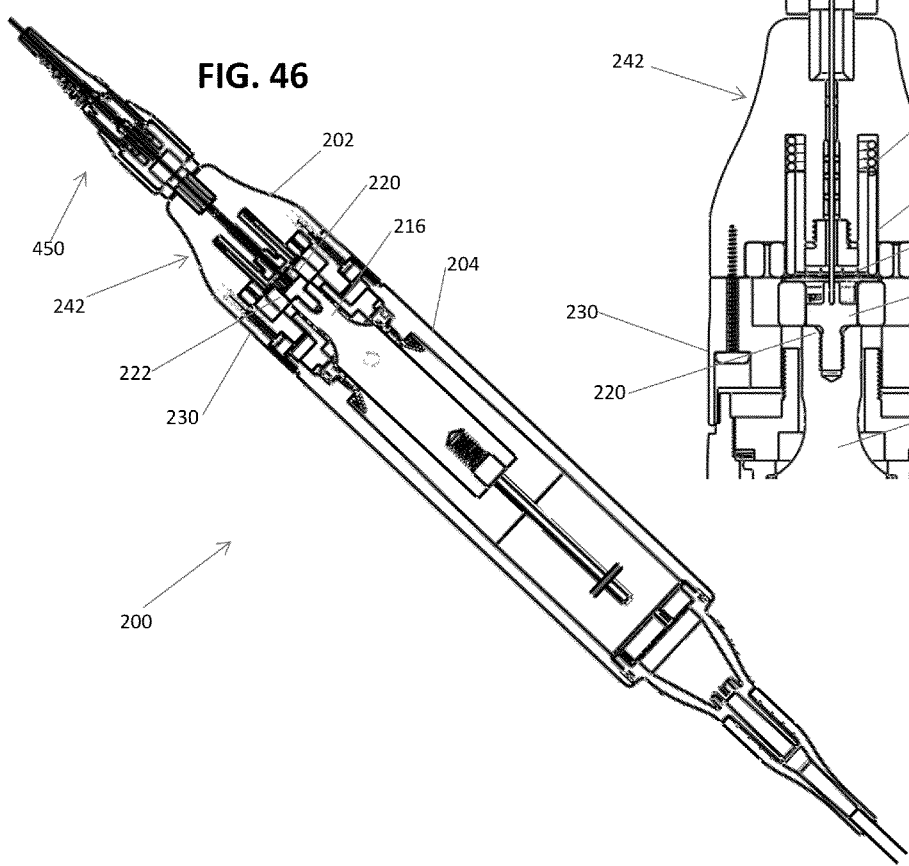
FIG. 46 is a cross-sectional view depicting a portion of the coupling system of FIG. 32, namely the transducer coupling, the middle housing, and the top housing illustrated in FIG. 32.

With reference to FIGS. 45 and 46, the middle housing 230 can be coupled to the top housing 242 with a snap fit coupling, an ultrasonic weld, a series of pins, or any suitable coupling. As shown in FIG. 33, the top housing 242 can define a third cavity 312 through which the waveguide 222 can pass. The third cavity 312 can be substantially coaxial with the first cavity 244 and the second cavity 248. As shown in FIG. 43, an upper portion 314 of the top housing 342 can define an orifice 316 through which the waveguide 222 can pass.

To assemble the coupling system 202, the transducer coupling 228 can be coupled to the transducer 204 with, for example, a threaded connection. In one example, the transducer coupling 228 can help retain the horn 216 within the transducer 204. The middle housing 230 can then be threaded onto the transducer housing 228 as further described herein. The lock 232 can be inserted into the middle housing 230 with the hinge assembly 276 in the closed position. As shown in FIG. 45, the middle housing 230 can be coupled to the top housing 242 with a snap fit, one or a plurality of pins, an ultrasonic weld, or any other suitable coupling such that the waveguide 222 can pass through the orifice 316.

As shown in FIG. 46, the coupling system 202 can be coupled to the transducer 204 by coupling the middle housing 230 with the transducer housing 228. In one embodiment, the transducer coupling 228 can include a threaded flange 227 and a threaded cylinder 225, as illustrated in FIG. 32, where the threaded cylinder 225 can define a first cavity 244. During assembly, the threaded cylinder 225 can be threadedly engaged with a threaded surface defined by the second cavity 248 of the middle housing 230. As the middle housing 230 is attached to the transducer housing 228, the connector 223 of the waveguide 222 can be concomitantly threaded into the connector 224 on the horn 216. In one example, the threaded cylinder 225 of the transducer housing 228 and the threaded portion 226 of the connector 223 can have the same thread pitch such that the coupling system 202 is connected to the transducer 204 at substantially the same time as the waveguide 222 is connected to the horn 216. In one embodiment, rotating the middle housing 230 can correspondingly rotate the hinge assembly 276, where rotating the hinge assembly 276 can correspondingly rotate the waveguide 222 such that the waveguide 222 is threadedly engaged with the horn 216. The middle housing 230 of the coupling system 202 can be threaded onto the transducer housing 208 until there is sufficient torque on the hinge assembly 276 to defeat, fracture, or disengage the frangible member 306. In one example, the torque sufficient to defeat the frangible member can be from about 10 to about 25 inch pounds (in lbs), from about 10 to about 15 in lbs, or from about 20 to about 25 in lbs. Once the frangible member 306 is defeated, the first arm 234 and the second arm 236 of the hinge assembly 276 can expand radially outward to an open position such that rotation of the middle housing 230 relative to the transducer housing 228 no longer correspondingly rotates the waveguide 222.

Figure 47:
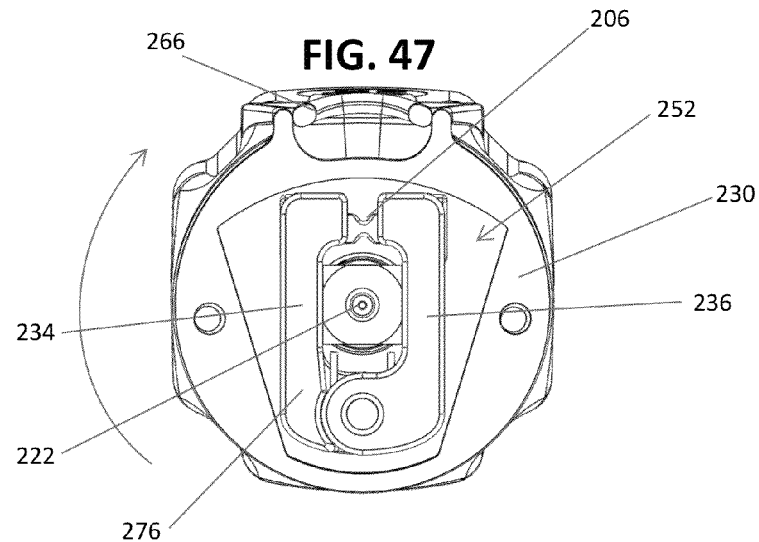
FIG. 47 is a top, partial cross-sectional view of the coupling system of FIG. 32, shown with a rotational force applied to the middle housing and the first arm and the second arm being depicted in a closed position.
Figure 48:
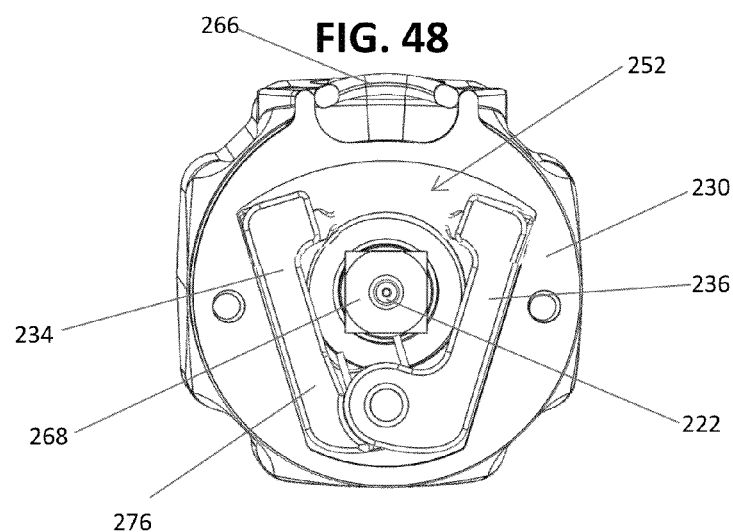
FIG. 48 is a top, partial cross-sectional view of the coupling system of FIG. 32, shown with the torque transmission element shown fractured and the first arm and the second arm extended radially outward into an open position.

FIGS. 47-49 depict one embodiment of a method for securing the waveguide 222 to the horn 316 with a predetermined amount of torque. Providing a torque limiting system and method can provide for a secure attachment between the waveguide 222 and the horn 316 that can obviate the need for a separate torque wrench. FIG. 47 depicts one version of the hinge assembly 276 in a closed position as a user rotates the middle housing 230. With the hinge assembly 276 in the closed position, the hinge assembly 276 can engage the flange 268 of the waveguide 222 such that the flange 268 can correspondingly rotate with the hinge assembly 276. Torque applied to the hinge assembly 276 can stress the frangible portion 306, where torque sufficient to break the frangible portion 306 can be achieved when the waveguide 222 is appropriately threaded onto the horn 216, as shown in FIG. 48.

When the frangible portion 306 is defeated, the first arm 234 and the second arm 236 of the hinge assembly 276 can pivot away from the waveguide 222 to the open position, as shown in FIG. 48, such that rotation of the middle housing 230 no longer torques the waveguide 222. In one embodiment, the frangible portion 306 can be configured to break or otherwise be defeated at a level of torque corresponding to a suitable connection between the waveguide 222 and the horn 316. In this manner, the waveguide 222 can be securely attached to the horn 316 without a separate tool and without relying upon a user to make a determination as to whether the components of the ultrasonic medical device 200 are suitably engaged. As shown in FIG. 48, when the hinge assembly 276 is in the open position, the first arm 234 and the second arm 236 can be spaced apart such that the arms do not contact the waveguide 222 during use of the ultrasonic medical device 200. The recess 252 can be configured and sized to allow the first arm 234 and the second arm 236 to expand radially such that they do not contact the waveguide 222 or the flange 268, where contact between the arms 234, 236 and the waveguide 222 may interfere with the transmission of any ultrasonic vibration. The recess 252 can also be configured and sized to prevent pieces of the frangible link 238 from separating from the hinge assembly 276, where pieces of the frangible link 238 may disrupt the operation of the coupling system 202 if they are unrestrained. In one example, the recess 252 can closely approximate the path of the first arm 234 and the second arm 236 during the transition from the closed position to the open position such that pieces of the frangible link 238 are retained by the hinge assembly 276. The frangible link 238 can be attached to the hinge assembly 276 with a snap fit, an adhesive, or other coupling mechanism that retains the pieces of the frangible link 238 after the frangible portion 306 is defeated.

Figure 50:
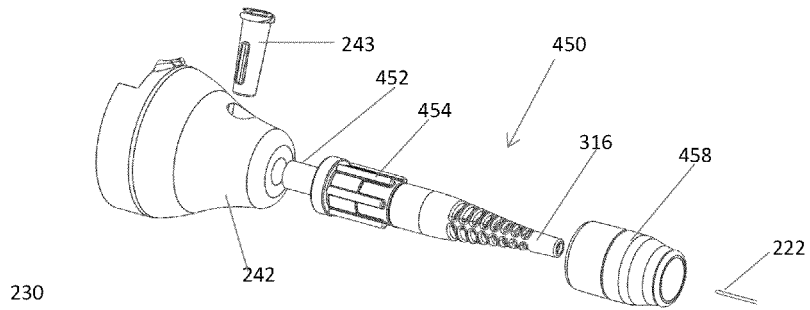
FIG. 50 is a perspective view of the top housing of the coupling system of FIG. 32 shown with a catheter attachment.

FIG. 50 depicts one embodiment of a catheter attachment 450 that can be coupled with the top housing 242 of the ultrasonic medical device 200. The catheter attachment 450 can include a coupling cylinder 452 that can be fixedly attached to the top housing 242. The catheter attachment 450 can include a sleeve 454 that can be rotatable relative to the coupling cylinder 252 such that a catheter (not shown) can be rotated by a user during a use (for example, during a procedure). A flexible portion 316 can facilitate a wide range of motion for an attached catheter without straining the catheter attachment 450 and a grip sleeve 458 can be provided that can cover the sleeve 454, where the grip sleeve 458 can be suitably textured to facilitate a user's grip when rotating the distal end of the catheter attachment 450. In one example, the top housing 242 can include a connector 243 (for example, a luer connector), which can facilitate the delivery or removal of fluid or the like through the ultrasonic medical device 200 and attached catheter (not shown).

Figure 49A:
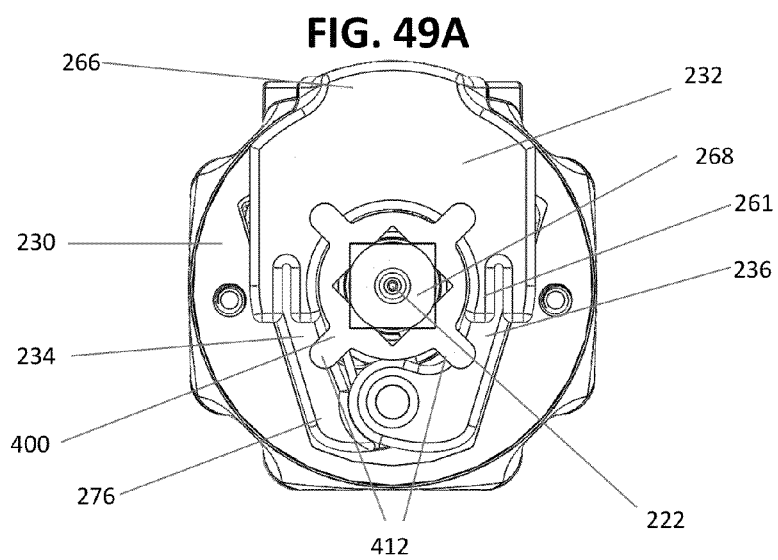
FIG. 49A is a top, partial cross-sectional view of the coupling system of FIG. 32, shown with the lock in a first position and the wrench spaced apart from the flange of the waveguide.

After use of the ultrasonic medical device 200, for example in a lithotripsy or vascular procedure, the waveguide 222 can be removed from the horn 216. FIGS. 49A-49B and FIGS. 51-52 illustrate one embodiment of a method that can include removing the lock 232 to allow the wrench 400, which can be initially positioned in a recess 404 defined by the top housing 242, to engage the flange 268 of the waveguide 222 such that the waveguide 222 can be decoupled from the horn 216. In FIGS. 49A and 51, the frangible portion 306 has been defeated and the hinge assembly 276 is shown in the open position. The lock 232 can be positioned such that it prevents the wrench 400, which can be biased proximally by a spring 402 housed within the recess 404, from translating proximally to engage the flange 268 of the waveguide 222. The tab 266 of the lock 232 can be pulled by a user to remove the lock 232 partially or completely from the ultrasonic medical device 200 such that the wrench 400 can engage the flange 268.

Figure 49B:
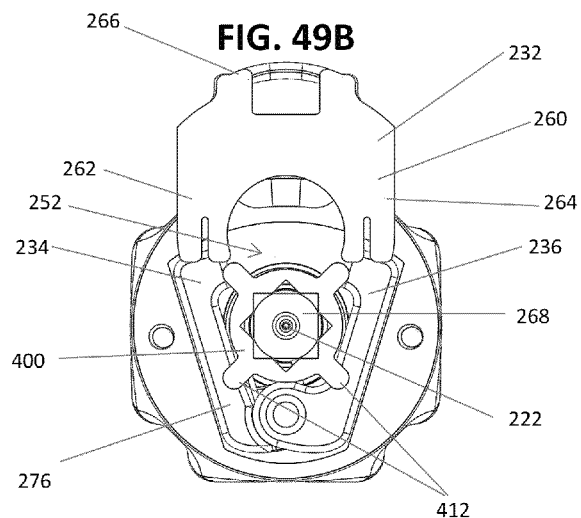
FIG. 49B is a top, partial cross-sectional view of the coupling system of FIG. 32, shown with the lock in a second position and the wrench engaged with the flange of the waveguide.
Figure 53:
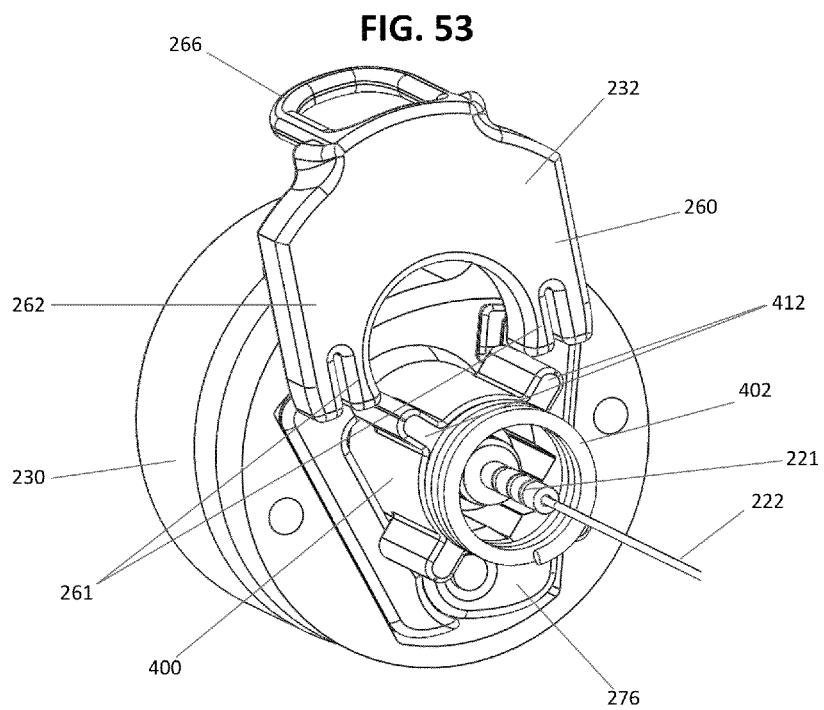
FIG. 53 is a perspective view of a portion of the coupling system of FIG. 32, shown with the lock partially removed and the wrench engaging the flange of the waveguide.

With reference to FIGS. 49B, 52, and 53, the lock 232 is shown removed from the ultrasonic medical device 200 such that the wrench 400, which can be biased proximally by the spring 402, can engage the flange 268 of the waveguide 222. Upon engagement of the wrench 400 with the flange 268, the middle housing 230 can be rotated to disengage the waveguide 222 from the horn 216. In one embodiment, when the hinge assembly 276 is in the open position, the waveguide 222 can only be disengaged from the horn 216 after the user removes the lock 232. As shown in FIG. 53, the radial projections 412 of the wrench 400 can engage the first arm 234 and the second arm 236 of the hinge assembly 276 and the multi-faceted inner cavity 410 of the wrench 400 can engage the flange 268 of the waveguide. Once the inner cavity 410 of the wrench 400 is engaged with the flange 268, rotation of the middle housing 240 can correspondingly rotate the flange 268 such that the waveguide 222 can be removed from the horn 216.

The foregoing description of embodiments and examples has been presented for purposes of illustration and description. It is not intended to be exhaustive or limiting to the forms described. Numerous modifications are possible in light of the above teachings. Some of those modifications have been discussed, and others will be understood by those skilled in the art. The embodiments were chosen and described in order to best illustrate principles of various embodiments as are suited to particular uses contemplated. The scope is, of course, not limited to the examples set forth herein, but can be employed in any number of applications and equivalent devices by those of ordinary skill in the art.

What is claimed is:

1. An ultrasonic medical device, comprising:
a transducer configured to convert an electrical drive signal to mechanical motion at an ultrasonic frequency, the transducer having a first connector;
a waveguide having a proximal end and a distal end, the proximal end having a second connector configured to mate with the first connector, the waveguide configured to receive the mechanical motion from the transducer and propagate the mechanical motion along the waveguide; and
a coupling system comprising a frangible link, the coupling system being configured to attach the second connector of the waveguide to the first connector of the transducer, wherein the frangible link is fractured when a predetermined torque limit is reached
wherein the coupling system further comprises a hinge assembly having a first position and a second position and
wherein the hinge assembly comprises a first arm and a second arm connected by the frangible link.

2. The ultrasonic medical device of claim 1, wherein the predetermined torque limit is 10-25 in-lbs.

3. The ultrasonic medical device of claim 1, wherein the waveguide is configured for a vascular procedure.

4. The ultrasonic medical device of claim 1, wherein the coupling system further comprises a lock and a wrench, wherein the lock and the wrench are configured to facilitate disassembly of the coupling system and the waveguide from the transducer.

5. The ultrasonic medical device of claim 4, wherein the wrench is configured to engage the second connector of the waveguide when the lock is moved from a first position to a second position.

6. An ultrasonic medical device, comprising:
a transducer configured to convert an electrical drive signal to mechanical motion at an ultrasonic frequency, the transducer having a first connector;
a waveguide having a proximal waveguide end and a distal waveguide end, the proximal waveguide end having a second connector configured to mate with the first connector, the waveguide configured to receive the mechanical motion from the transducer and propagate the mechanical motion along the waveguide; and a coupling system comprising a hinge assembly, the hinge assembly being configured to torque the second connector of the waveguide to the first connector of the transducer, wherein the hinge assembly is configured to transition from a first position to a second position when a predetermined torque limit is reached wherein the hinge assembly comprises a first arm and a second arm connected by a frangible link having a frangible portion.

7. The ultrasonic medical device of claim 1, wherein the predetermined torque limit is 10-25 in-lbs.

8. The ultrasonic medical device of claim 6, wherein the waveguide is configured for a vascular procedure.

9. The ultrasonic medical device of claim 6, wherein the coupling system further comprises a lock and a wrench, wherein the lock and the wrench are configured to facilitate disassembly of the coupling system and the waveguide from the transducer.

10. The ultrasonic medical device of claim 9, wherein the wrench is biased by a bias spring, the bias spring being configured to engage the wrench with the second connector of the waveguide when the lock is moved from a first position to a second position.

11. An ultrasonic medical device, comprising:
- a transducer configured to convert an electrical drive signal to mechanical motion at an ultrasonic frequency, the transducer having a first connector;
- a waveguide having a proximal waveguide end and a distal waveguide end, the proximal waveguide end having a second connector configured to mate with the first connector, the waveguide configured to receive the mechanical motion from the transducer and propagate the mechanical motion along the waveguide;
- a coupling system comprising a hinge assembly having a frangible link, the hinge assembly being configured to torque the second connector of the waveguide to the first connector of the transducer, wherein the hinge assembly is configured to transition from a first position to a second position when the frangible link is fractured.

12. The ultrasonic medical device of claim 1, wherein the predetermined torque limit is 10-25 in-lbs.

13. The ultrasonic medical device of claim 11, wherein the hinge assembly comprises a first arm and a second arm connected by the frangible link having a frangible portion.

14. The ultrasonic medical device of claim 11, wherein the waveguide is configured for a vascular procedure.

15. The ultrasonic medical device of claim 11, wherein the coupling system further comprises a lock and a wrench, wherein the lock and the wrench are configured to facilitate disassembly of the coupling system and the waveguide from the transducer.

16. The ultrasonic medical device of claim 15, wherein the wrench is configured to engage the second connector of the waveguide when the lock is moved from a first position to a second position.

17. The ultrasonic medical device of claim 11, further comprising an outer probe coaxial with the waveguide.

* * * * *